US00PP34401P2

(12) United States Plant Patent
Infante Espiñeira

(10) Patent No.: US PP34,401 P2
(45) Date of Patent: Jul. 5, 2022

(54) NECTARINE TREE NAMED 'ANDES NEC-6'

(50) Latin Name: ***Prunus persica* var. *nucipersica* (Nectarine)**
Varietal Denomination: Andes Nec-6

(71) Applicants: VIVEROS ASOCIADOS CHILE LIMITADA, Santiago (CL); UNIVERSIDAD DE CHILE, Santiago (CL)

(72) Inventor: Rodrigo Infante Espiñeira, Santiago (CL)

(73) Assignees: VIVEROS ASOCIADOS CHILE LIMITADA, Santiago (CL); UNIVERSIDAD DE CHILE, Santiago (CL)

( * ) Notice: Subject to any disclaimer, the term of this patent is extended or adjusted under 35 U.S.C. 154(b) by 0 days.

(21) Appl. No.: 17/306,048

(22) Filed: May 3, 2021

(51) Int. Cl.
*A01H 5/08* (2018.01)
*A01H 6/74* (2018.01)

(52) U.S. Cl.
USPC ..... Plt./188

(58) Field of Classification Search
USPC ..... Plt./188
CPC ..... A01H 5/08; A01H 5/0856; A01H 5/00; A01H 6/74; A01H 6/7454
See application file for complete search history.

(56) References Cited

U.S. PATENT DOCUMENTS

| | | | | |
|---|---|---|---|---|
| PP2,794 P * | 2/1968 | Anderson | | Plt./192 |
| PP3,165 P * | 5/1972 | Anderson | | Plt./192 |
| PP7,918 P * | 7/1992 | Bradford | | Plt./192 |
| PP10,286 P * | 3/1998 | Zaiger | | Plt./197 |
| PP26,838 P2 * | 6/2016 | Zaiger | A01H 6/7463 | Plt./195 |
| PP28,019 P3 * | 5/2017 | Byrne | | Plt./197 |
| PP29,705 P3 * | 9/2018 | Infante Espineira | A01H 6/7454 | Plt./188 |

* cited by examiner

*Primary Examiner* — June Hwu
(74) *Attorney, Agent, or Firm* — Greer, Burns & Crain, Ltd

(57) ABSTRACT

A new and distinct variety of nectarine tree named 'Andes Nec-6' with medium vigor, which produces a nectarine with a slow pulp softening rate during the last two weeks before a commercial harvest, the nectarine has a high postharvest life potential, the nectarine is broad elliptic, moderately asymmetric, the nectarine has white flesh and the surface of its skin is cream yellow with 70 to 80% of its skin being covered by mottled red blush, and the nectarine has a balanced acid/sweet flavor.

5 Drawing Sheets

Latin name: *Prunus persica* var. *nucipersica* (Nectarine).
Variety denomination: ANDES NEC-6.

BACKGROUND

This new cultivar resulted from controlled hybridization between nectarine 'Ruby Diamond' (U.S. Plant Pat. No. 7,918P), (♀) and nectarine 'IFF 389' (not patented) (♂) performed in 2011 at Maipú, Metropolitan Region, Chile (latitude −33° 78'S, longitude −70° 64'S, altitude 210 m above level). This tree was first asexually propagated through grafting on 'Nemaguard' rootstock in the same field in July of 2013 and tested on a block of 10 cloned trees in the same experimental station at Maipú and in El Tambo, VI region of Chile.

SUMMARY

The new variety 'Andes Nec-6' has a white flesh while the variety 'Ruby Diamond' (U.S. Plant Pat. No. 7,918P) has a yellow flesh, bearing both big fruits. Regarding the male progenitor, the white fleshed nectarine 'IFF 389', its size barely reaches 110 g while 'Andes Nec-6' reaches up to 300 g.

New variety 'Andes Nec-6' differs from variety 'Ruby Diamond' (U.S. Plant Pat. No. 7,918P) in part because 'Andes Nec-6' has a crenate leaf blade margin whereas 'Ruby Diamond' has a finely serrate leaf blade margin, in contrast nectarine 'IFF 389' has a smooth margin. The shape of fruit of new variety 'Andes Nec-6' is broad elliptic whereas the shape of fruit of 'Ruby Diamond' (U.S. Plant Pat. No. 7,918P) is uniform, very symmetrical, globose with some slight truncation at the base. In comparison, 'Ruby Diamond' (U.S. Plant Pat. No. 7,918P) has an earlier harvest period of 10 days before 'Andes Nec-6', and the nectarine 'IFF 389' ripens 15 days after 'Andes Nec-6'. In comparison, 'Andes Nec-4' (U.S. Plant Pat. No. 29,705) has an earlier harvest period, and it ripens 25 days before 'Andes Nec-6'.

Distinctive characteristics of 'Andes Nec-6' include its upright to spreading plant habit with medium vigor. The fruit is broad elliptic, moderately asymmetric, the flesh color is white, and the surface of the skin is cream yellow, covered by 70 to 80% mottled red blush.

This cultivar main feature is a slow flesh softening rate during the last two weeks before the commercial harvest. This feature enables delaying harvesting, pursuing an increase of the fruit size and soluble solids content without affecting their postharvest life potential. Secondly, 'Andes Nec-6' has a high postharvest life potential, which can reach up to 40 days at 0° C. while maintaining its initial sensory quality. Regarding 'Ruby Diamond' (U.S. Plant Pat. No. 7,918P), its postharvest life potential can barely reach up to 21 days at 0° C. From a sensory point of view this is a variety of balanced sweetness/acidity ratio and in general an average overall sensory quality. The variety 'Andes Nec-6' is not susceptible to "chilling injury" and therefore, can be used for exporting to distant markets.

BRIEF DESCRIPTION OF THE DRAWINGS

The drawings of the nectarine of the present variety are color photographs.

DETAILED BOTANICAL DESCRIPTION—CHARACTERIZATION OF 'ANDES NEC-6' NECTARINE

Figure 1:
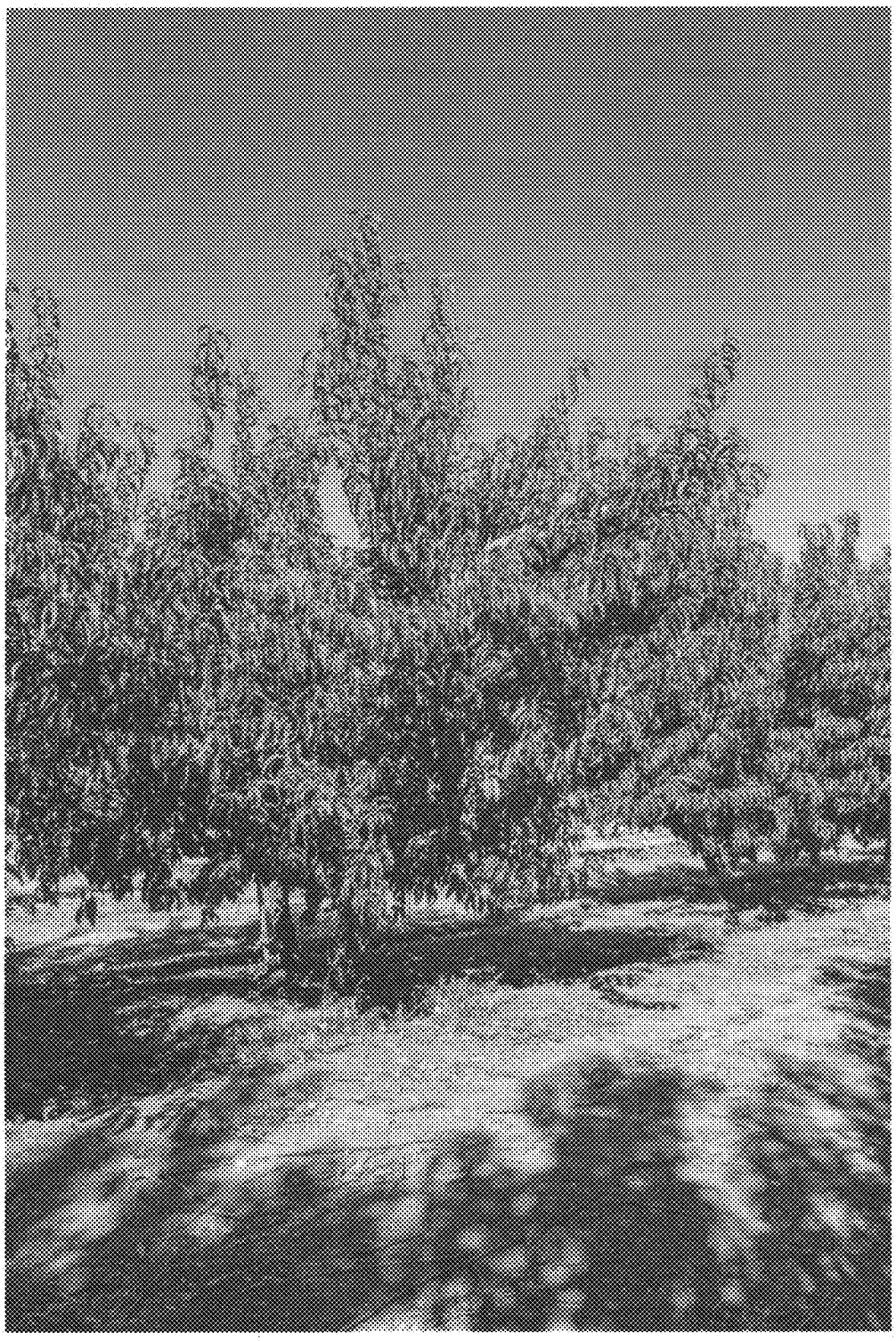
FIG. 1 shows a 7-year old nectarine tree named 'Andes Nec-6'.
Figure 2:
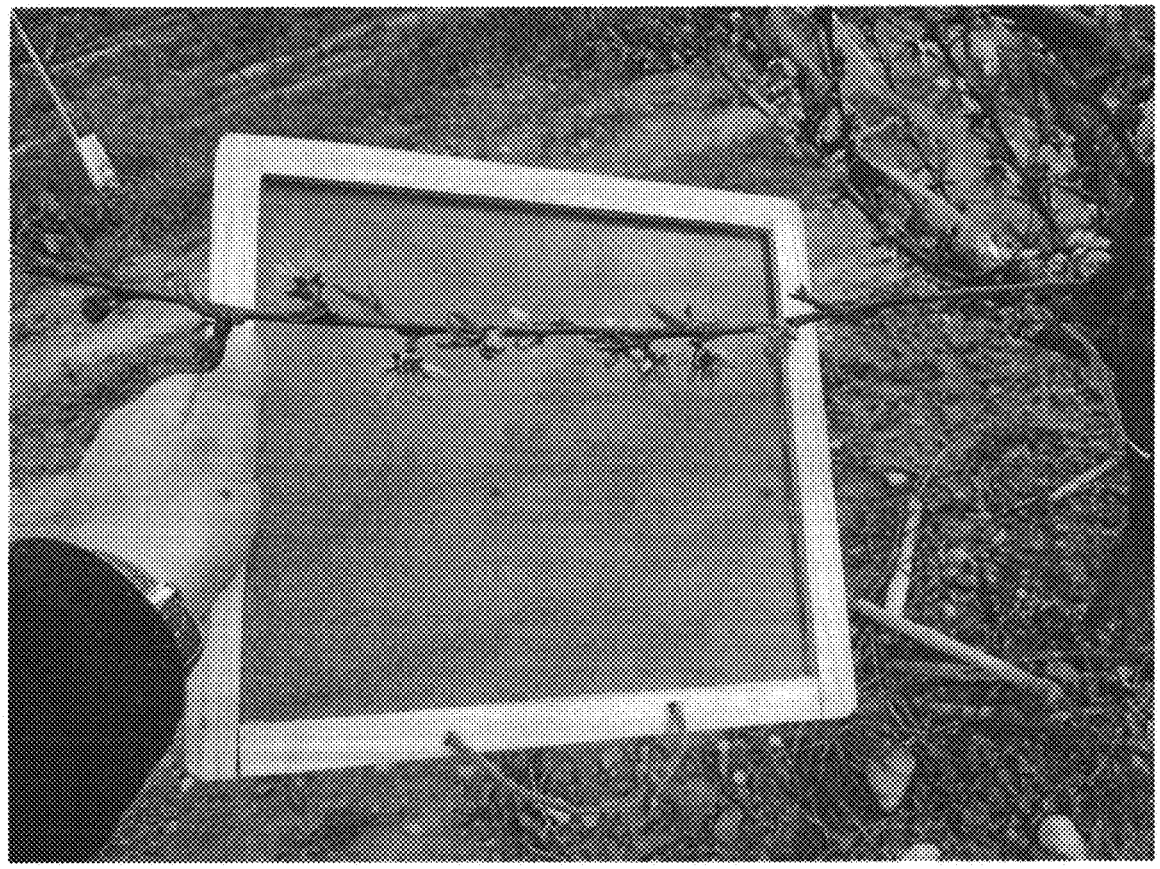
FIG. 2 shows typical specimens of a flower.
Figure 3:
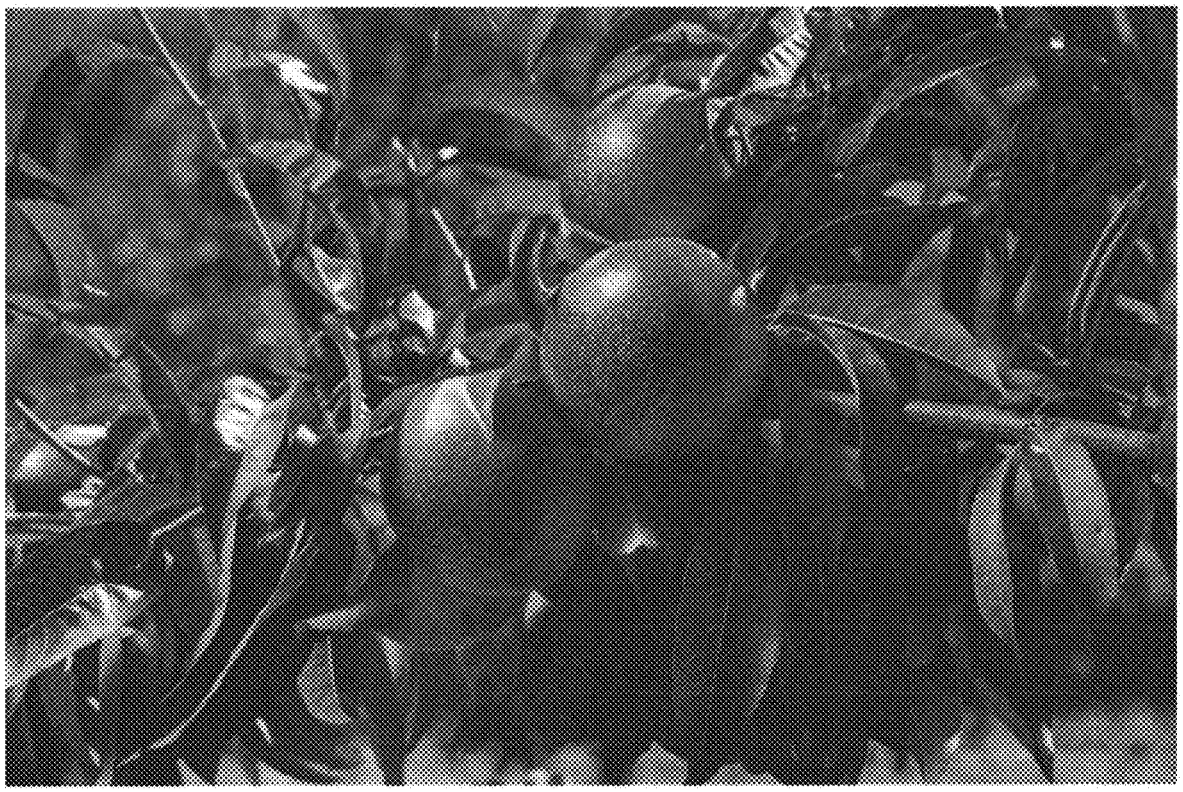
FIG. 3 shows typical specimens of fruit and leaves on a nectarine tree named 'Andes Nec-6'.
Figure 4:
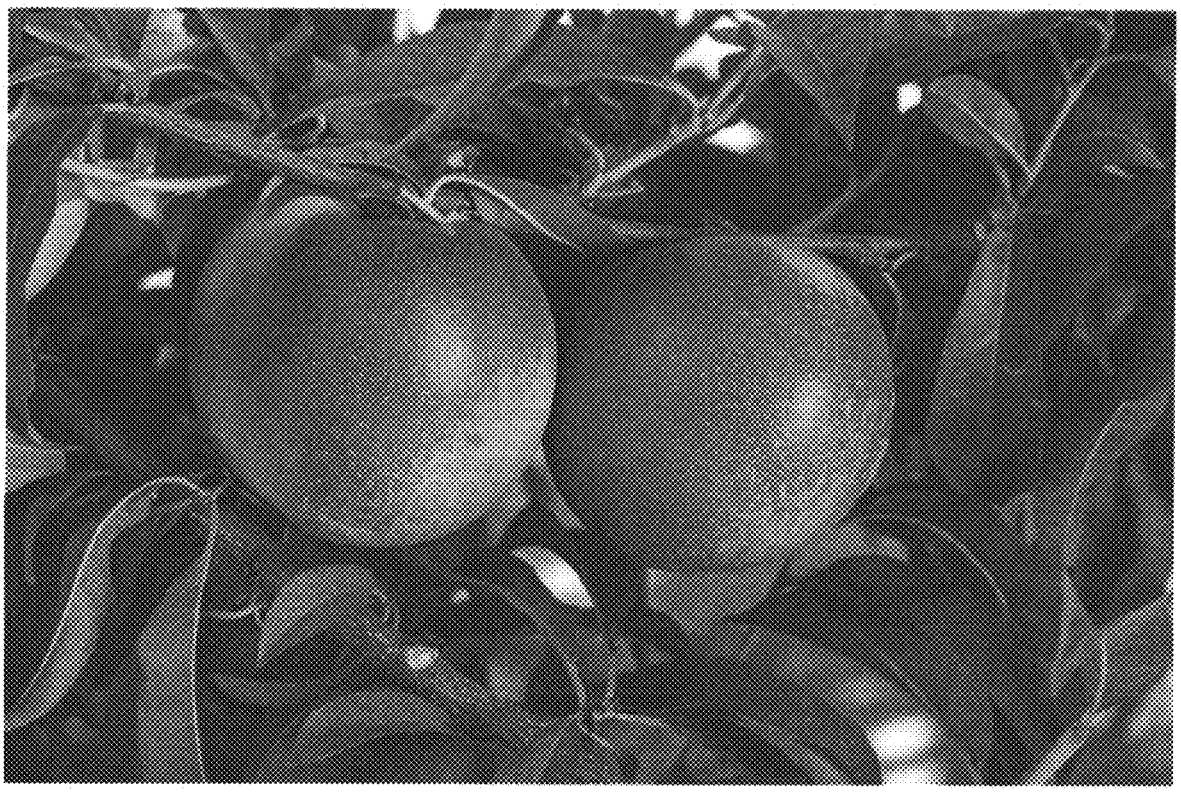
FIG. 4 shows an enlarged view of the fruit and leaves of the tree of FIG. 3.
Figure 5:
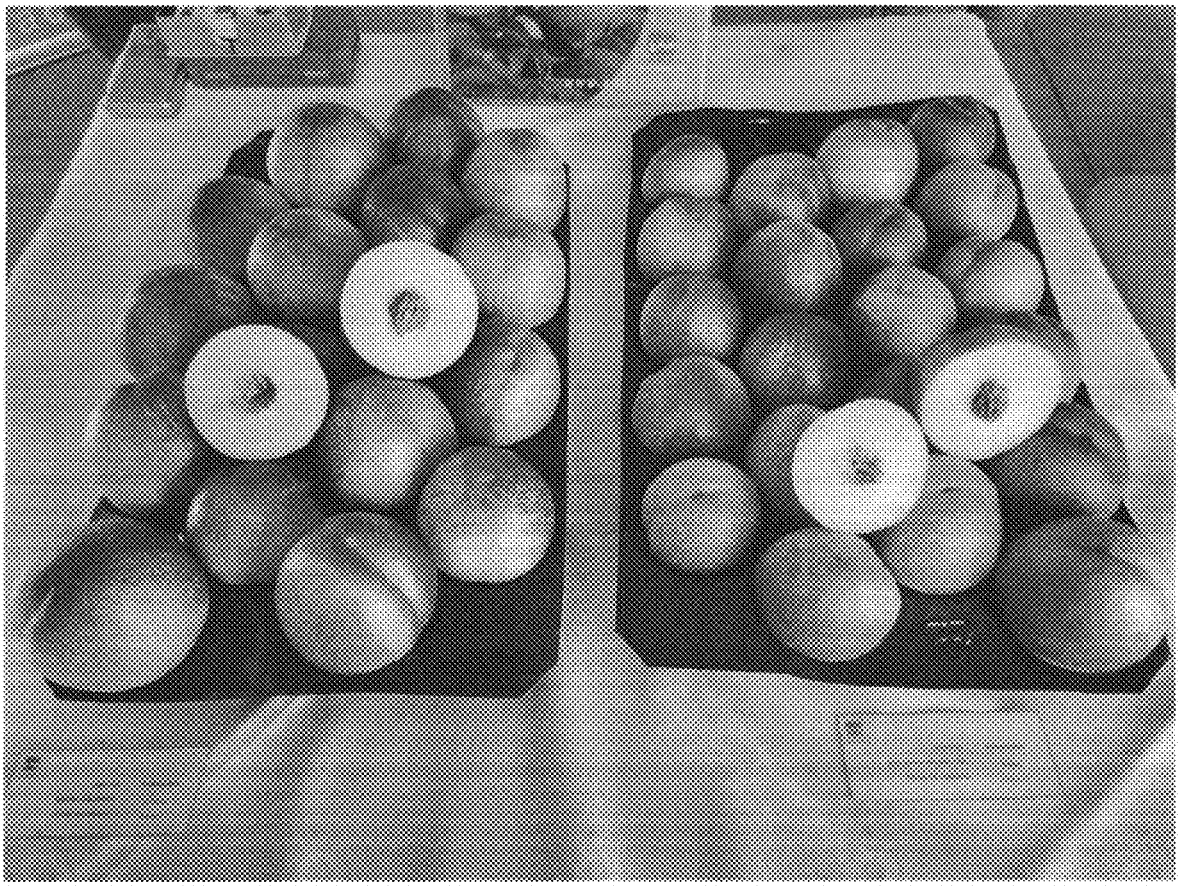
FIG. 5 shows the fruit flesh and the stone of 'Andes Nec-6'.

Color descriptions below are based on evaluations with a Minolta CR-400 colorimeter al CIE D65/0° illumination/viewer conditions. The color parameters correspond to the uniform color space CIELAB, derived from McGuire (1992). Two color coordinates, a* and b*, as well as a psychometric index of lightness, L*, are defined. The L* is a measurement of luminosity, i.e., the equivalence of each color on the gray scale, ranging from 0 (black) to 100 (White). The a* takes positive values (0 to +60) for reddish colors and negative values (0 to −60) for the greenish ones, whereas the b* takes positive values (0 to +60) for yellowish colors and negative values (0 to −60) for the bluish ones. This is a much more precise and repeatable analysis of color than can be obtained by using color charts. Where a reasonably close match could be discerned, The Munsell Color Chart is also referenced.

Tree:

1. *Size*.—Medium, similar to 'Robin' (Not patented). An 8-year-old tree is 2.5-3.0 m high shaped as an open vase, 2.5-3.0 of diameter.
2. *Vigor*.—Medium, similar to 'Robin' (Not patented). Shoots reach 30 to 70 cm of width on regular spring/summer growing period.
3. *Habit*.—Upright to spreading, like 'Albertina' (Not patented). It is well adapted to open vase training.
4. *Flowering shoot thickness* (*excluding brindilles*).—Medium, similar to 'Redhaven' (Not patented). The typical and observed flowering shoot diameter is 8.5-10.5 mm.
5. *Flowering shoot length of internodes*.—Medium, similar to 'Redhaven' (Not patented). The typical and observed flowering shoot internode length is 3.0-4.5 cm.
6. *Flowering shoot coloration*.—There is present anthocyanin coloration in the zone exposed to sunlight, reaching a light red color, that in coordinates a*, b* and L* of the CIELab space color (McGuire, 1992) corresponds to 44.7, 11.0, and 11.2, respectively, but in the lower part of the shoot the anthocyanin coloration is weak, similar to 'Springtime' (Not patented), reaching a light brown color, that in coordinates a*, b* and L* of the CIELab space color (McGuire, 1992) corresponds to 36.8, 7.6, and 12.0, respectively. (McGuire, R. G. 1992. Reporting of Objective Color Measurements. Hortscience. 27(12): 1254-1255).
7. *Flowering shoot density of flower buds*.—Weak, similar to 'Springtime' (Not patented), reaching in an average year 20-25 flowers/100 cm long shoot.
8. *Flowering shoot*.—General distribution of flower buds: In groups of two or more, similar to 'Redhaven' (Not patented).
9. The trunk of an 8-year old tree, grafted on Nemaguard (Not patented) rootstock, shows a 12-14 cm diameter, measured on 50 cm above the ground, the bark texture is rough with many lenticels, and the bark color is dark brown, that in coordinates a*, b* and L* of the CIELab space color (McGuire, 1992) corresponds to 44.3, 3.7, and 9.1, respectively.
10. The primary branches diameter reaches 7-9 cm in an 8-year old tree, and the color is light brown, that in coordinates a*, b* and L* of the CIELab space color (McGuire, 1992) corresponds to 48.6, −2.7, and 22.5, respectively.
11. *Vegetative buds shape and color*.—Acuminate, 5.0-7.5 mm length, color brown that in coordinates a*, b* and L* of the CIELab space color (McGuire, 1992) corresponds to 98.2, −5.5, and 28.6, respectively.

Flower:

12. *Type*.—Rosette, similar to 'Robin' (Not patented), reaching a whole diameter of 2.0 to 2.5 cm, and ovary is settled 0.4 to 0.6 cm low the calyx.
13. *Calyx color of inner side* (*opened flower, before falling of petals*).—Pale yellow, similar to 'Robin' (Not patented), the color is classified as in coordinates a*, b* and L* of the CIELab space color (McGuire, 1992) corresponds to 58.2, 11.3, and 25.5, respectively.
14. *Corolla predominant color* (*inner side*).—Medium pink, similar to 'Fuzalode' (Not patented), classified in coordinates a*, b* and L* of the CIELab space color (McGuire, 1992) corresponds to 86.2, −2.1, and 10.5, respectively.
15. *Petal shape*.—Medium elliptic, similar to 'Bradgust' (Not patented).
16. *Petal size*.—Medium, similar to 'Robin' (Not patented), 0.8 to 1.2 cm diameter.
17. *Petals number*.—Five, similar to 'Redhaven' (Not patented).
18. *Stamens position compared to petals*.—Above 0.3 to 0.5 cm, similar to 'Redhaven' (Not patented).
19. *Stamen number and length*.—There are 25-35 stamens per flower with the average 0.8 cm length, of white-cream color, in coordinates a*, b* and L* of the CIELab space color (McGuire, 1992) corresponds to 90.3, −3.2, and 9.0, respectively.
20. *Stigma position compared to anthers*.—Above, similar to 'Fuzalode' (Not patented).
21. *Pistil*.—There is normally 1 per flower, 10-12 mm length and white cream color according to in coordinates a*, b* and L* of the CIELab space color (McGuire, 1992) corresponds to 61.2, 3.5, and 9.9, respectively.

22. *Anthers pollen*.—Present and abundant, similar to 'Redhaven' (Not patented), and the characteristic color is classified in coordinates a*, b* and L* of the CIELab space color (McGuire, 1992) corresponds to 85.1, 4.3, and 42.5, respectively.
23. *Ovary color and surface texture*.—Pubescence is absent, similar to 'Fuzalode' (Not patented), green color classified in coordinates a*, b* and L* of the CIELab space color (McGuire, 1992) corresponds to 36.2, −87.1, and −16.1, respectively.

Leaf:

24. *Leaf blade length*.—Long, reaching 12-15.5 cm long. New variety 'Andes Nec-6' differs from variety 'Andes Nec-4' (U.S. Plant Pat. No. 29,705) in part because 'Andes Nec-6' has a crenate leaf blade margin whereas 'Andes Nec-4' has a shallow serrate leaf blade margin.
25. *Leaf blade width*.—Broad, reaching 3.5-4.5 cm width.
26. *Leaf blade*.—Ratio length/width: Low, similar to 'Mountaingold' (Not patented), reaching a ratio of 3.3.
27. *Leaf blade shape in cross section*.—Concave, similar to 'Merrill Gemfree' (Not patented).
28. *Leaf blade curvature of apex*.—Absent, similar to 'Merril Sundance' (Not patented).
29. *Leaf blade angle at base*.—Acute, less than 90°, similar to 'Springtime' (Not patented).
30. *Leaf blade angle at apex*.—Small, similar to 'Red June' (Not patented).
31. *Leaf blade color*.—Medium Green, similar to 'Robin' (Not patented), classified in coordinates a*, b* and L* of the CIELab space color (McGuire, 1992) corresponds to 37.5, −8.2, and −16.1, respectively on the upper surface and in coordinates a*, b* and L* of the CIELab space color (McGuire, 1992) corresponds to 56.8, −5.1, and −10.0, respectively, in the lower surface.
32. *Petiole length*.—Medium, similar to 'Genadix-7' (Not patented), reaching 0.7-1.0 cm.
33. *Petiole*.—Two nectaries present, similar to 'Redhaven' (Not patented).
34. *Petiole shape of nectaries*.—Round, similar to 'Springtime' (Not patented).
35. *Petiole predominant number of nectaries*.—Two.
36. *Stipule length*.—Short, similar to 'Redhaven' (Not patented), 10-12 mm length.
37. *Stipule color* (*upper and lower surfaces*).—Medium Green, classified in coordinates a*, b* and L* of the CIELab space color (McGuire, 1992) corresponds to 37.5, −8.2, and −16.1, respectively on the upper surface and in coordinates a*, b* and L* of the CIELab space color (McGuire, 1992) corresponds to 56.8, −5.1, and −10.0, respectively, in the lower surface.

Fruit:

38. *Fruit size*.—Large, similar to 'Loring', ranging between 200 to 250 g.
39. *Fruit shape* (*in ventral view*).—Broad elliptic, similar to 'Cavalier' (Not patented). The observed fruit length parallel to the suture is 6.0 to 7.2 cm and width perpendicular to the suture is 6.5 to 7.5 cm. The shape of fruit of new variety 'Andes Nec-6' is broad elliptic whereas the shape of fruit of 'Andes Nec-4' is circular.
40. *Fruit shape of pistil end*.—Weakly depressed, similar to 'Robin' (Not patented).
41. *Fruit symmetry* (*viewed from pistil end*).—Moderately asymmetric, similar to 'Brittney Lane' (U.S. Plant Pat. No. 10,286).
42. *Fruit prominence of suture*.—Weak, similar to 'Redhaven' (Not patented).
43. *Fruit depth of stalk cavity*.—Medium, similar to 'Triumph' (Not patented), ranging between 6-8 mm.
44. *Fruit width of stalk cavity*.—Medium, similar to 'May Grand' (U.S. Plant Pat. No. 2,794). 1.5-2.0 cm.
45. *Fruit ground color*.—Cream yellow, classified in coordinates a*, b* and L* of the CIELab space color (McGuire, 1992) corresponds to 60.1, 6.2, and 30.0, respectively, similar to 'Fuzalode' (Not patented) when is mature.
46. *Fruit over color*.—Present.
47. *Fruit*.—Hue of over color: 27.0. medium Red, classified as CIELAB, similar to 'Red Diamond' (U.S. Plant Pat. No. 3,165).
48. *Fruit pattern of over color*.—Mottled, similar to 'Merrill Sundance' (Not patented).
49. *Fruit extent of over color*.—Large, reaching 70-80%.
50. *Fruit pubescence*.—Absent.
51. *Fruit thickness of skin*.—Thick, similar to 'Carman' (Not patented).
52. *Fruit adherence of skin to flesh*.—Strong, similar 'Babygold 5' (Not patented).
53. *Fruit firmness of pulp*.—Firm.
54. *Fruit carotenoid coloration of flesh*.—Cream white, classified in coordinates L, Hue and Chroma of the CIELab space color (McGuire, 1992) corresponds to 79.4, 64.5 and 16.6, respectively.
55. *Fruit anthocyanin coloration directly under skin*.—Absent.
56. *Fruit anthocyanin coloration of flesh*.—Absent.
57. *Fruit anthocyanin coloration around stone*.—Medium, similar to 'Ryans Sun' (Not patented).
58. *Fruit texture of the flesh*.—Not fibrous, melting flesh type, similar to 'Redhaven' (Not patented).
59. *Fruit sweetness*.—High, reaching 17-19%.
60. *Fruit acidity*.—Low, ranging between 0.5 to 0.9% malic acid when fruit is ripe.
61. The conspicuousness of lenticels of the fruit is strong.

Stone:

62. *Stone size compared to fruit*.—Large ranging between 11 to 15 g.
63. *Stone shape* (*in lateral view*).—Elliptic, similar to 'Loring'. The length is 3.8 cm and width 2.2 cm.
64. *Stone intensity of brown color*.—Very strong, classified as in coordinates a*, b* and L* of the CIELab space color (McGuire, 1992) corresponds to 26.9, 15.9, and 6.3, respectively.
65. *Stone relief of surface*.—Equally pits and grooves.
66. *Stone grooves*.—Similar to 'Madame Girard' (Not patented).
67. *Stone tendency of splitting* (*at peak harvest*).—Absent.
68. *Stone adherence to flesh*.—Present, similar to 'Sweet Gold' (Not patented).

69. *Stone degree of adherence to flesh*.—Weak, similar to 'Dixired' (Not patented).

Phenology:

70. *Time of leaf bud burst*.—Medium, similar to 'Redhaven' (Not patented). On Southern Hemisphere is between 10th to 25th September.
71. *Time of beginning of flowering*.—Medium, similar to 'Redhaven' (Not patented). On Southern Hemisphere is between 25th to 30th August.
72. *Duration of flowering*.—Short, 5-7 days.
73. *Time of maturity for consumption*.—Medium, similar to 'Fairhaven' (Not patented). On Southern Hemisphere is between 15th to 20th January.
74. *Tendency to preharvest*.—Absent.
75. *Pest/disease resistance/susceptibility*.—This genotype is not genetically resistant to any common pest and disease of peach, as Mildew (*Mildiú*), leaf curl (Enrrollamiento de la hoja, Cloca, *Taphrina deformans*), bacterial canker (Cáncer bacterial, Bacteria *Pseudomona syringae*), aphids (pulgones), thrips (trips) or, Oriental moth (Polilla de la fruta oriental, *Cydia molesta*).
76. *Fruit characterization is in table* 1.—

TABLE 1

Fruit characterization of nectarine 'Andes Nec-6'

| Season | Harvest Date | Blush % | Equatorial Diameter (mm) | Firmness (Lb)* Equatorial | Firmness (Lb)* Shoulders | Firmness (Lb)* Suture | Firmness (Lb)* Fruit Tip | Soluble Solids (*Brix) |
|---|---|---|---|---|---|---|---|---|
| 2018-2019 | 11-Jan-19 | 70% | 80 | 13.2 | 10.6 | 11 | 13.7 | 17.7 |

TABLE 1-continued

Fruit characterization of nectarine 'Andes Nec-6'

| Season | Harvest Date | Blush % | Equatorial Diameter (mm) | Firmness (Lb)* Equatorial | Firmness (Lb)* Shoulders | Firmness (Lb)* Suture | Firmness (Lb)* Fruit Tip | Soluble Solids (*Brix) |
|---|---|---|---|---|---|---|---|---|
| 2019-2020 | 13-Jan-20 | 50% | 85 | 13 | 10.4 | 11.8 | 14.7 | 17.1 |
| 2020-2021 | 21-Jan-21 | 50% | >90 | 14.1 | 11.3 | 11.6 | 14 | 17.1 |

*Firmness measurements were performed with a penetrometer model A6510006 with an 8 mm tip.

GENERAL TECHNICAL NOTES

Very good outward appearance. High productivity. One plant can produce about 50 kilograms of fruit. Excellent flavor. After five years of evaluation, the variety continues to show its outstanding characteristics: very good productivity, good size, good flavor and good external appearance. The variety has a high potential for export to Asian countries because of its white flesh and its exceptional post-harvest life potential.

Having thus described and illustrated the new variety of nectarine tree, I claim:

1. A new and distinct variety of nectarine tree named 'Andes Nec-6', substantially as illustrated and described herein, and which produces a nectarine with a slow pulp softening rate during the last two weeks before a commercial harvest, the nectarine has a high postharvest life potential, the nectarine is broad elliptic, moderately asymmetric, the nectarine has white flesh and the surface of its skin is cream yellow with 70 to 80% of its skin being covered by mottled red blush, and the nectarine has a balanced acid/sweet flavor.

* * * * *